United States Patent [19]

Kim

[11] Patent Number: 4,547,525
[45] Date of Patent: Oct. 15, 1985

[54] REDUCING METHANE PRODUCTION IN FISCHER-TROPSCH REACTIONS

[75] Inventor: Chang J. Kim, Short Hills, N.J.

[73] Assignee: Exxon Research and Engineering Co., Florham Park, N.J.

[21] Appl. No.: 563,109

[22] Filed: Dec. 19, 1983

[51] Int. Cl.⁴ .............................................. C07C 1/04
[52] U.S. Cl. ................... 518/713; 518/715; 518/716
[58] Field of Search ............. 518/715, 728, 713, 719, 518/716

[56] References Cited

U.S. PATENT DOCUMENTS

| | | | |
|---|---|---|---|
| 2,549,111 | 4/1951 | Millendorf et al. | 518/728 |
| 2,595,096 | 4/1952 | Parker | 568/451 |
| 2,638,487 | 5/1953 | Russum et al. | 568/451 |
| 4,042,614 | 8/1977 | Vannice et al. | 518/715 |
| 4,451,679 | 5/1984 | Knifton et al. | 568/451 |

OTHER PUBLICATIONS

Storch et al., Fischer–Tropsch & Related Synthesis, John Wiley, New York, (1951), pp. 441–448.

Primary Examiner—Howard T. Mars
Attorney, Agent, or Firm—Edward M. Corcoran

[57] ABSTRACT

Methane production in catalytic Fischer-Tropsch hydrocarbon synthesis reactions is reduced by adding olefins to the $H_2$ and CO feed mixture. Alpha olefins of ten carbon atoms or less are particularly preferred.

18 Claims, No Drawings

REDUCING METHANE PRODUCTION IN FISCHER-TROPSCH REACTIONS

BACKGROUND OF THE INVENTION

1. Field of the Invention

This invention relates to reducing methane production in Fischer-Tropsch hydrocarbon synthesis reactions by adding olefins to the reactor feed. More particularly, this invention relates to reducing methane production in catalytic Fischer-Tropsch reactions wherein hydrocarbons are synthesized from a feed comprising a mixture of CO and $H_2$, by adding one or more olefins to the feed.

2. Background of the Invention

The production of hydrocarbons from mixtures of $H_2$ and CO via the Fischer-Tropsch process is well-known to those skilled in the art. As opposed to the well-known "methanization" process which produces methane as synthetic natural gas from mixtures of $H_2$ and CO, the Fischer-Tropsch process is more generally aimed at producing higher value products such as chemical feedstocks and liquid fuels. Thus, high methane make is undesirable in Fischer-Tropsch synthesis processes because it is a relatively low value product which is formed at the expense of more desirable products. It is also uneconomical to try to convert the so-formed methane back into a CO and $H_2$ mixture and recycle it back into the reactor.

Methane make in Fischer-Tropsch reactions is often expressed by a term known as methane selectivity. Methane selectivity can be defined by either of two methods. They are, (a) mole % $CH_4$ produced based on the amount of CO consumed or (b) weight % of $CH_4$ produced based on total hydrocarbon products formed.

Many different catalysts and processes have been disclosed for Fischer-Tropsch synthesis, some of which have extremely high methane make. Thus, U.S. Pat. No. 4,077,995 discloses synthesis of $C_1$–$C_4$ aliphatic hydrocarbons over a catalyst comprising a sulfided mixture of CoO, $Al_2O_3$ and ZnO while U.S. Pat. No. 4,039,302 discloses $C_1$–$C_3$ hydrocarbon production using a mixture of the oxides of Co, Al, Zn and Mo. U.S. Pat. No. 4,151,190 discloses producing $C_2$–$C_4$ hydrocarbons from mixtures of CO and $H_2$ using a supported catalyst comprising a metal oxide or sulfide of Mo, W, Re, Ru, Ni or Pt plus an alkali or alkaline earth metal, with Mo-K on carbon being preferred. U.S. Pat. Nos. 4,243,553 and 4,243,554 disclose $MoS_2$ as a Fischer-Tropsch catalyst. Many other catalysts are known to be useful for Fischer-Tropsch synthesis employing metals such as iron, copper, titania, etc. These are known to those skilled in the art.

The type of catalyst used and process conditions employed have an important bearing on $CH_4$ selectivity. For example, nickel gives a high $CH_4$ selectivity and is used mainly as a methanization catalyst. Methane selectivity usually increases with increasing temperature, decreasing pressure and increasing the $H_2$/CO ratio of the feed. Accordingly, process conditions are selected so as to minimize $CH_4$ selectivity while maintaining a relatively high reaction rate as is well known to those skilled in the art.

It is known that $CH_4$ selectivity is influenced by the choice of promoter and support, such as alkali metal promotersreducing $CH_4$ selectivities of iron catalysts. It is also known in the art that noble metals such as ruthenium supported on inorganic refractory oxide supports exhibit superior hydrocarbon synthesis characteristics with relatively low methane production. Thus, U.S. Pat. No. 4,088,671 suggests minimizing methane production by using a small amount of Ru on a cobalt catalyst. Examples of supported ruthenium catalysts suitable for hydrocarbon synthesis via Fischer-Tropsch reactions are disclosed in U.S. Pat. Nos. 4,042,614 and 4,171,320 the disclosures of which are incorporated herein by reference. It is also known that the type of support used also influences methane production. In the case of supported ruthenium catalysts, the use of a titania or titania containing support will result in lower methane production than, for example a silica, alumina or manganese oxide support.

Those skilled in the art recognize the need for reducing methane production still further, even when employing catalysts comprising ruthenium supported on titania.

SUMMARY OF THE INVENTION

It has now been discovered that methane production in Fischer-Tropsch hydrocarbon synthesis reactions is reduced by adding one or more olefins to the $H_2$ and CO gas feed. Thus, the instant invention relates to a process for reducing methane production in Fischer-Tropsch processes wherein hydrocarbons are synthesized from feeds comprising mixtures of CO and $H_2$, by adding at least one olefin to the feed. In a preferred embodiment the olefin or olefins will comprise one or more $C_2$–$C_{10}$ alpha olefins, with an olefin to CO mole ratio of from about 1/10 to ¾ and the catalyst will comprise at least one Group VIII metal supported on an inorganic refractory oxide support. In a particularly preferred embodiment, the catalyst will comprise ruthenium supported on titania.

DETAILED DESCRIPTION OF THE INVENTION

Preferred olefins useful in the process of the instant invention include alpha olefins of the type R—CH=$CH_2$ wherein R is hydrogen or an alkyl group. Still more preferable are $C_2$–$C_{10}$ alpha olefins. The amount of olefin added to the CO/$H_2$ gas feed mixture will, on an olefin to CO mole ratio, broadly range from about 1/100 to 5/1 and more preferably from about 1/10 to ¾.

Although the process of the instant invention may be practiced in the presence of any suitable Fischer-Tropsch catalyst, in a preferred embodiment it will be practiced in the presence of a catalyst comprising one or more Group VIII metals supported on an inorganic refractory oxide support, preferably ruthenium supported on such a support. Thus, suitable supports include oxides of titania, niobia, vanadium, tantalum, silica, alumina, manganese, and mixtures thereof. Preferably the catalyst support will be selected from the group consisting of titania, zirconium titanate, mixtures of titania and alumina, mixtures of titania and silica, alkaline earth titanates, alkali titanates, rare earth titanates and mixtures of any one of the foregoing with supports selected from the group consisting of vanadia, niobia, tantala, alumina, silica, and mixtures thereof. Thus, in a particularly preferred embodiment of this invention the process will be carried out in the presence of a catalyst comprising ruthenium supported on a titania support.

In general, the amount of catalytic metal present on the catalyst will generally range from about 0.01 to 50 weight percent of the total catalyst composition, preferably from about 0.1 to 5.0 weight percent and still more preferably from about 0.5 to 5 weight percent.

In general, in the process of this invention the temperature will broadly range from about 100° to 500° C. and preferably from about 200° to 300° C. at a pressure of 100 to 10,000 kPa and preferably 500 to 5,000 kPa. The space velocity of the feed gas will range from about 10 to 10,000 standard cm$^3$/hr-cm$^3$ of catalyst and preferably 100–4,000. The hydrogen to carbon monoxide mole ratio of the feed gas, $H_2$/CO, will range from about 0.5 to 10 and preferably from about 1 to 3.

The invention will be more readily understood by reference to the following examples.

EXAMPLES

EXAMPLE 1

In this experiment a catalyst consisting of 1.2 wt. % of ruthenium supported on titania was prepared by impregnating a titania support material with an aqueous solution of ruthenium nitrate dissolved in acetone using the incipient wetness technique. The titania support material was Degussa's P-25 titanian dioxide which x-ray diffraction analysis revealed was 75% anatase titania and 25% rutile titania. It should be noted that prior to impregnation the titania support material was manually pelletized and then crushed and meshed to give catalyst particles in an 80–140 mesh (Tyler) particle size. Following impregnation, the acetone was evaporated at room temperature and the so-formed impregnate reduced in flowing hydrogen for 4 hours at 450° C., followed by a passivation in air to produce the final catalyst. Three grams of this ruthenium-titania catalyst and 12 g of 80–100 mesh quartz powder diluent were charged into a $\frac{3}{8}$" OD stainless steel down-flow tubular reactor and contacted with flowing hydrogen for 4 hours at 390° C.

The Fischer-Tropsch reaction was conducted with a 2/1 mole ratio of $H_2$/CO containing 4 percent $N_2$. The small amount of nitrogen diluent was added for the purpose of being an internal standard for a subsequent on-line GC analysis of the product. The gaseous feed mixture was passed over the catalyst at a rate of 55 standard cm$^3$/min. at a temperature of 200° C. and partial pressure of $H_2$ and CO at 3.32 atmospheres and 1.68 atmospheres, respectively. The reaction products and extent of CO conversion were constantly monitored using two on-line GC sampling valves. A hot sampling valve encased in a hot box at the exit of the reactor was used to determine hydrocarbon product distribution in the $C_1$–$C_{30}$ range. The hydrocarbon product distribution was determined using a Tenax GC column programmed at 50°14 330° C. employing a flame ionization detector. A cold sampling valve was located at the exit of the reactor (after a cold trap) to determine the extent of CO conversion as well as the amounts of $CH_4$, $CO_2$, ethylene, ethane, propylene and propane produced by the reaction. The amounts of these gases produced were determined using Molecular Sieve 5A and Porapak R columns employing both flame ionization and thermoconductivity detectors by means of column switching valves.

At steady state operating conditions, the CO conversion level was 8.4 mole percent and the $CH_4$ selectivity, defined as 100 × moles of $CH_4$ produced per mole of CO converted was 6.4 mole percent. To this steady state reaction system, ethylene was introduced at a rate of 4.5 standard cm$^3$/min and the total pressure adjusted to keep the $H_2$ and CO partial pressures unchanged. This ethylene addition, corresponding to 8.2 mole percent of the CO/$H_2$ feed (24 percent of the CO), reduced the $CH_4$ selectivity from 6.4 percent down to 3.5 percent with little effect on the extent of CO conversion as set forth in the following table.

| % Ethylene based on $H_2$/CO feed | 0 | 8.2 |
|---|---|---|
| % CO conversion | 8.4 | 9.0 |
| % $CH_4$ selectivity* | 6.4 | 3.5 |

Note:
$100 \times \frac{\text{moles } CH_4 \text{ produced}}{\text{mole of CO reacted}}$ This example demonstrates the reduction of methane make in Fischer-Tropsch hydrocarbon synthesis reactions when an olefin (ethylene) is added to the $H_2$/CO feed.

EXAMPLE 2

This experiment was similar to that of Example 1, except that the amount of ethylene added to the feed was increased to 20 mole percent (based on the $H_2$/CO feed). The measured $CH_4$ selectivity as a result of this increased ethylene addition was 2.7 percent, which corresponds to a 59 percent reduction in $CH_4$ make from the base case.

EXAMPLE 3

This experiment was similar to Examples 1 and 2, except that the olefin added to the reaction mixture was 1-decene. This was added at a liquid rate of 1.15 cm$^3$/hr. using a micro high pressure pump to the reactor which had been operating at the steady-state Fischer-Tropsch reaction conditions of Example 1. About 4 mole percent of the 1-decene was added based on the $H_2$/CO which reduced the $CH_4$ make by 20 percent.

EXAMPLE 4

This experiment illustrates the effect of olefin addition to the $H_2$/CO feed in a Fischer-Tropsch hydrocarbon synthesis reaction employing an iron-based catalyst.

This experiment employed a precipitated, bulk iron catalyst containing copper, potassium and silicon, similar to the composite described by Frohning (C. D. Frohning, "Fischer-Tropsch Synthese, Chemierohstoffe aus Kohle," J. Falbe ed., Stuttgart, Thieme, 1977). Ten grams of this catalyst (80–100 mesh, Tyler) and 10 g of the powdered pyrex diluent were charged to the fixed-bed, down-flow stainless steel tubular reactor described in Example 1. The charged catalyst was reduced in $H_2$ for 2 hours at 200° C. and the Fischer-Tropsch reaction conducted at a temperature of 200° C., partial pressure of hydrogen of 3.32 atmospheres and partial pressure of CO of 1.68 atmospheres. The flow rate of the $H_2$/CO gas feed was 100 standard cm$^3$/min. After four days on stream, the steady-state CO conversion level was 14.1 percent of which 12.7 percent were converted to hydrocarbon products and the remaining 1.4 percent to $CO_2$. The amount of $CH_4$ produced was 1.4 moles based on 100 moles of CO converted to hydrocarbon products.

Ethylene in an amount of 9.6 percent based on the $H_2$/CO feed was added to the steady-state reaction system while maintaining all the other conditions constant. The partial pressures of the feed gas constituents with the ethylene addition were $H_2$-3.32 atm., CO-1.68 atm. and ethylene 0.48 atm. The CO conversion level was substantially unchanged at 15.1 percent (13.9 percent to hydrocarbon products and 1.2 percent to $CO_2$), but the amount of $CH_4$ produced was significantly reduced. That is, 1 mole of $CH_4$ was produced per 100 moles of CO converted to hydrocarbon products. This amounted to a 30 percent reduction in the $CH_4$ selectivity (make) with the iron catalyst.

What is claimed is:

1. A process for reducing methane formation in a Fischer-Tropsch process for synthesizing hydrocarbons which comprises contacting, at an elevated temperature of 100°-500° C. and a pressure of from about 100-10,000 kPa, a $H_2$/CO feed mixture with a heterogeneous catalyst comprising one or more Group VIII metals supported on an inorganic refractory oxide support for a time sufficient to produce hydrocarbons, including methane, wherein one or more olefins is added to the $H_2$/CO feed mixture in an amount sufficient to reduce said methane formation to a level lower than it would be without adding said olefin to said feed.

2. The process of claim 1 wherein one or more olefins are added to said feed in an amount, based on an olefin to CO mole ratio, ranging from about 1/100 to 5/1.

3. The process of claim 2 wherein said olefin comprises one or more alpha olefins.

4. The process of claim 3 wherein said alpha olefin is of the type $R-CH=CH_2$.

5. The process of claim 4 wherein R is hydrogen or an alkyl group.

6. The process of claim 5 wherein said olefin comprises one or more $C_2$-$C_{10}$ alpha olefins.

7. The process of claim 6 wherein said olefin to CO mole ratio ranges from about 1/10-$\frac{3}{4}$.

8. The process of claim 7 wherein the temperature of said process ranges from about 200°-300° C.

9. The process of claim 8 wherein the mole ratio of $H_2$ to CO in the gas feed ranges from about 0.5 to 10.

10. A process for reducing methane formation in a Fischer-Tropsch process for synthesizing hydrocarbons which comprises contacting, at an elevated temperature of 100°-500° C. and a pressure of from 100-10,000 kPa, a gas feed comprising a mixture of $H_2$ and CO with a heterogeneous catalyst comprising ruthenium supported on an inorganic refractory oxide support for a time sufficient to produce hydrocarbons, including methane, wherein one or more olefins is added to the $H_2$/CO feed mixture in an amount sufficient to reduce said methane formation to a level lower than it would be without adding said olefin to said feed.

11. The process of claim 10 wherein said olefin comprises at least one alpha olefin.

12. The process of claim 11 wherein said alpha olefin is of the type $R-CH=CH_2$ wherein R is hydrogen or an alkyl group.

13. The process of claim 11 wherein said olefin comprises a $C_2$-$C_{10}$ alpha olefin.

14. The process of either of claim 11 or 12 wherein the amount of olefin present, on an olefin to CO mole ratio, ranges from about 1/100 to 5/1.

15. The process of claim 14 wherein said temperature ranges from about 200°-300° C.

16. The process of claim 10 wherein the mole ratio of $H_2$ to CO of the feed ranges from about 0.5 to 10.

17. The process of any of claims 1, 5 or 9 wherein said supported Group VIII metal comprises iron combined with copper and potassium.

18. The process of any of claims 10, 12 or 15 wherein said catalyst support comprises titanium dioxide.

* * * * *